United States Patent
Goodman (12)

(10) Patent No.: US 6,358,541 B1
(45) Date of Patent: Mar. 19, 2002

(54) TOPICAL PREPARATION FOR THE TREATMENT OF HAIR LOSS

(75) Inventor: David S. Goodman, 721 Woodhavin La., Naples, FL (US) 34108

(73) Assignee: David S. Goodman, Naples, FL (US)

( * ) Notice: Subject to any disclaimer, the term of this patent is extended or adjusted under 35 U.S.C. 154(b) by 0 days.

(21) Appl. No.: 09/563,555

(22) Filed: May 3, 2000

(51) Int. Cl.$^7$ .......................... A01N 65/00; A61K 35/78; A61K 39/385; A61K 7/06

(52) U.S. Cl. .......................... 424/727; 424/74; 424/70.1; 424/725

(58) Field of Search .......................... 424/195.1, 613, 424/401, 727, 725, 417, 426, 419, 484, 486, 489, 490, 497, 70.1, 74; 514/356, 474, 880

(56) References Cited

U.S. PATENT DOCUMENTS

| | | | |
|---|---|---|---|
| 4,863,898 A | 9/1989 | Ashmead et al. | 514/6 |
| 5,624,673 A | 4/1997 | Bonte et al. | 424/195 |
| 5,650,171 A | 7/1997 | Quigley, Jr. et al. | 424/486 |
| 5,652,266 A | 7/1997 | Bobier-Rival et al. | 514/557 |
| 5,653,983 A | 8/1997 | Meybeck et al. | 424/195 |
| 5,663,160 A | 9/1997 | Meybeck et al. | 514/182 |
| 5,700,483 A | 12/1997 | Quigley, Jr. et al. | 424/486 |
| 5,750,108 A * | 5/1998 | Edwards | 424/195.1 |
| 5,972,345 A | 10/1999 | Chizick et al. | 424/195 |
| 5,989,536 A * | 11/1999 | Deckner et al. | 424/78.05 |
| 5,997,853 A | 12/1999 | Bolich, Jr. et al. | 424/70 |
| 6,075,056 A * | 6/2000 | Quigley, Jr. et al. | 514/649 |

FOREIGN PATENT DOCUMENTS

| | | | | |
|---|---|---|---|---|
| AU | WO99/20250 | 4/1999 | .......... | A61K/31/57 |
| GB | WO96/27376 | 9/1996 | ............ | A61K/9/12 |

OTHER PUBLICATIONS

Zatz Skin Delivery of Retinoids: Reducing the Skin Irritancy of Topical Retinoids; http://www.rci.rutgers.eud/~zatz/Skin-Permeation/Retinoids.html, 1998.*
J. A. Duke, The Green Pharmacy, Rodale Press, Emmaus, PA: 78–80 (1997).
G. F. Webster, Topical Tretinoin in Acne Therapy, J. Am. Acad. of Dermatol., 39(2 Pt 3): S38–S43 (1998).
B. Shroot, Pharmacodynamics and Pharmacokinetics of Topical Adapalene, J. Am. Acad. Dermatol., 39(2 Pt 3): S17–S24 (1998).
N. V. Perricone et al., Photoprotective and Antiinflammatory Effects of Topical Glycolic Acid, Dermatol. Surg., 22(5): 435–437 (1996).
J. W. Fluhr et al., Tolerance Profile of Retinol, Retinaldehyde and Retinoic Acid Under Maximized and Long–Term Clinical Conditions, Dermatol., 199, Suppl. 1: 57–60 (1999).

M. C. Spellman et al., Efficacy and Safety of Azelaic Acid and Glycolic Acid Combination Therapy Compared with Tretinoin Therapy for Acne, Clin. Ther., 20(4): 711–721 (1998).
L. V. Allen, Jr., The Basics of Compounding, Int. J. Pharm. Comp., 3(5):385–389 (1999).
T. J. Franz et al., Betamoethasone Valerate Foam 0.12%: A Novel Vehicle with Enhanced Delivery and Efficacy, Int. J. Dermatol., 38: 628–632 (1999).
W. F. Bergfeld, Retinoids and Hair Growth, J. Am. Acad. Dermatol., 39(2 Pt 3): S86–S89 (1998).
L. Fort–Lacoste et al., Comedolytic Effect of Topical Retinaldehyde in the Rhino Mouse Model, Dermatol., 199, Suppl. 1: 33–35 (1999).
D. Piacquadio et al., The Critical Role of the Vehicle to Therapeutic Efficacy and Patient Compliance, J. Am. Acad. Dermatol., 39(2 Pt 3): S67–S73 (1998).
F. C. Lowe et al., Phytotherapy in the Treatment of Benign Prostatic Hyperplasia: An Update, Urology, 53: 671–678 (1999).
R. Odom, Managing Actinic Keratoses with Retinoids, J. Am. Acad. Dermatol., 39(2 Pt 3): S74–S78 (1998).
E. F. Sherertz et al., Topical Tretinoin Enhances Percutaneous Absorption of 5–Fluorouracil In Vitro, J. Am. Acad. Dermatol., 17(4): 692–694 (1987).
E. J. Van Scott et al., Alpha Hydroxy Acids: Procedures for Use in Clinical Practice, Cutis, 43(3): 222–228 (1989).
E. J. Van Scott et al., Hyperkeratinization, Corneocyte Cohesion, and Alpha Hydroxy Acids, J. Am. Acad. Dermatol., 11(5 Pt 1): 867–879 (1984).
D. O. Thueson et al., The Roles of pH and Concentration in Lactic Acid–induced Stimulation of Epidermal Turnover, Dermatol. Surg., 24(6): 641–645 (1998).
A. N. Lin et al., Salicylic Acid Revisited, Int. J. Dermatol., 37(5): 335–342 (1998).
M. Loden et al., Distribution and Keratolytic Effect of Salicylic Acid and Urea in Human Skin, Skin Pharmacol., 8(4): 173–178 (1995).
B. Gabard et al., Salicylic Acid and Urea—Possible Modification of the keratolytic Effect of Salicylic Acid by Urea, Hautarzt., 40, Suppl. 9: 71–73 (1989). Abstract Only.

(List continued on next page.)

*Primary Examiner*—Jon P. Weber
*Assistant Examiner*—Patricia Patten
(74) *Attorney, Agent, or Firm*—Robert I. Pearlman; Riker, Danzig, Scherer, Hyland & Perretti LLP

(57) ABSTRACT

Improved preparations for the treatment of androgenetic alopecia comprise saw palmetto berry extract containing phytosterols and one or more low irritability constituents that enhance penetration of the extract into hair follicular pores. The low irritability penetration enhancer(s) may be selected from the group consisting of adapalene, tretinoin, retinaldehyde, tazarotene, salicylic acid, azelaic acid, and glycolic acid. Also provided is a method for reducing hair loss by application to the scalp of the improved preparations.

18 Claims, No Drawings

OTHER PUBLICATIONS

J. W. Quigley et al., Reduced Skin Irritation with Tretinoin Containing Polyoprepolymer–2, A New Topical Tretinoin Delivery System: A Summary of Preclinical and Clinical Investigations, J. Am. Acad. Dermatol., 38(4): S5–S10 (1998).

M. J. Skov et al., Topical Delivery System for Tretinoin: Research and Clinical Implications, J. Pharm. Sci., 86(10): 1138–1143 (1997).

J. J. Ferry et al., Influence of Tretinoin on the Percutaneous Absorption of Minoxidil from an Aqueous Topical Solution, Clin. Pharmacol. Ther., 47(4): 439–446 (1990).

M. Duvic, Pharmacologic Profile of Tazarotene, Cutis, 61(2 Suppl.): 22–26 (1998).

M. Duvic et al., The Pathogenesis of Psoriasis and the Mechanism of Action of Tazarotene, J. Am. Acad. Dermatol., 39(4 Pt 2): S129–S133 (1998).

H. Stege et al., Topical Application of Tazarotene in the Treatment of Nonerythrodermic Lamellar Ichthyosis, Arch Dermatol, 134(5): 640–641 (1998).

R. H. Foster et al., Tazarotene, Drugs, 55(5): 705–711 (1998).

J. J. Leyden, Topical Treatment of Acne Vulgaris: Retinoids and Cutaneous Irritation, J. Am. Acad. Dermatol., 38(4): S1–S4 (1998).

R. Marks, Clinical Safety of Tazarotene in the Treatment of Plaque Psoriasis, J. Am. Acad. Dermatol., 37(2 Pt 3): S25–S32 (1997).

M. Duvic et al., Molecular Mechanisms of Tazarotene Action in Psoriasis, J. Am. Acad. Dermatol., 37(2 Pt 3): S18–S24 (1997).

H. Gollnick et al., Topical Drug Treatment in Acne, Dermatology, 196(1): 119–125 (1998).

J. R. Gibson, Azelaic Acid 20% Cream (AZELEX®) and the Medical Management of Acne Vulgaris, Dermatol. Nurs., 9(5): 339–344 (1997).

P. S. Mackrides et al., Azelaic Acid Therapy for Acne [Published Erratum Appears In Am. Fam. Physician, 55(5): 1586 (1997)], Am. Fam. Physician, 54(8): 2457–2459 (1996).

C. W. Oh et al., An Ultrastrucural Study of the Retention Hyperkeratosis of Experimentally Induced Comedones in Rabbits: The Effects of Three Comedolytics, J. Dermatol., 23(3): 169–180 (1996).

K. Graupe et al., Efficacy and Safety of Topical Azelaic Acid (20 Percent Cream): An Overview of Results from European Clinical Trials and Experimental Reports, Cutis, 57(1 Suppl.): 20–35 (1996).

J. R. Gibson, Rationale for the Development of New Topical Treatments for Acne Vulgaris, Cutis, 57(1 Suppl.): 13–19 (1996).

G. S. Bazzano et al., Topical Tretinoin for Hair Growth Promotion, J. Am. Acad. Dermatol., 15(4 Pt 2): 880–883, (1986).

M. Goepel et al., Saw Palmetto Extracts and Noncompetitively Inhibit Human $\alpha_1$–Adrenoceptors In Vitro, Prostate, 38(3): 208–215 (1999).

J. C. Carraro et al., Comparison of Phytotherapy (Permixon®) with Finasteride in the Treatment of Benign prostate Hyperplasia: A Randomized International Study of 1,098 Patients, Prostate, 29(4): 231–240 (1996).

F. C. Lowe, Saw Palmetto Berry in the Treatment of Benign Prostatic Hyperplasia, Clin. Res. Regul. Aff., 14(1): 53–66 (1997).

G. L. Plosker et al., Serenoa Repens (Permixon®) A Review of its Pharmacology and Therapeutic Efficacy in Benign Prostatic Hyperplasia, Drugs Aging, 9(5): 379–395 (1996).

L. Ravenna et al., Effects of the Lipidosterolic Extract of Serenoa Repens (Permixon®) on Human Prostatic Cell Lines, Prostate, 29(4): 219–230 (1996).

C. Iehle et al., Human Porstatic Steroid 5 Alpha–Reductase Isoforms—A Comparative Study of Selective Inhibitors, J. Steroid Biochem. Mol. Biol., 54(5–6): 273–279 (1995).

C. W. Bayne et al., Effect of Permixon In–Vitro Co–Culture Model for BPH, Urological Research, 25(1): 90 (1997).

M. Magdy El–Sheikh et al., The Effect of Permixon on Androgen Receptors, Acta. Obstet. Gynecol. Scand., 67: 397–399 (1988).

F. Di Silverio et al., Evidence that Serenoa Repens Extract Displays an Antiestrogenic Activity in Prostatic Tissue of Benign Prostatic Hypertrophy Patients, Eur. Urol., 21: 309–314 (1992).

G. Champault et al., Medical Treatment of the Prostatic Adenomia: A Controlled Test of PA 109 {Permixon: Serenoa Repens Extract} vs. Placebo in 100 Patients, Ann. Urol., 6: 407–410 (1984). Abstract Only pp. Oct. 17, 2000.

T. J. Wilt et al., Saw Palmetto Extracts for Treatment of Benign Prostatic Hyperplasia: A Systematic Review [published eratum appears in JAMA, 281(6): 515 (1999)] JAMA, 280(18): 1604–1609 (1998).

* cited by examiner

TOPICAL PREPARATION FOR THE TREATMENT OF HAIR LOSS

BACKGROUND OF THE INVENTION

1. Field of the Invention

This invention relates to an improved preparation and method for treating androgenetic alopecia; and more particularly to a preparation comprising an active extract of saw palmetto berries and a compound which exhibits low irritability and enhances penetration of the extract into hair follicular pores.

2. Description of the Prior Art

Human hair undergoes a normal growth cycle, known as the pilar cycle where each hair grows continuously for about 2 to 4 years, stops growing for 2 to 4 months, and then falls out. In its place, healthy new hair begins to grow, thereby restarting the cycle. Androgen receptors located in the hair follicle and sebaceous gland sensitize hair follicles to androgens. There is evidence that the pilar cycle of hair follicles on the scalp respond to higher levels of androgens by displaying shortened growth phases, and by displaying a greater fraction of increasingly thinner and shorter hairs.

Saw palmetto (serenoa repens) is a small berry-bearing palm native to the southeast United States. Saw palmetto berry extract ("SPBE") has been shown to block 5-alpha reductase, the enzyme that converts the hormone testosterone into dihydrotestosterone ("DHT"), the major androgen implicated in changes in the pilar cycle. This enzyme also blocks the binding of DHT to androgen receptors. Thus, in treating the balding scalp, SPBE may act by blocking the formation of DHT, by inhibiting binding of DHT to the androgen receptors, or both. The use of SPBE in reducing hair loss is well known and has been cited for example in "The Green Pharmacy", pp. 78–79, Rodale Press, Emmaus, Penn., 1996.

In U.S. Pat. No. 5,972,345, SPBE has been combined with the extracts of African Pygeum and stinging nettle to produce a formulation for administration to the scalp for the treatment of male pattern hair loss. Stinging nettle extract is a known rubefacient that may open the follicle entrance by producing irritation.

In U.S. Pat. No. 5,750,108, SPBE is administered to the scalp as the third step in a procedure comprising lengthy, sequential preparatory treatments, first with tea tree oil, and then with an acidic solution of chlorine dioxide. The purpose of these preparatory treatments is to remove sebum from the follicle entrance and improve the effectiveness of the SBPE. However, chlorine dioxide is an irritant and an extremely hazardous material. The Occupational Safety and Health Administration of the U.S. Department of Labor, in a list published by Government Institutes, Inc. Rockville, Md., 1990, shows a Permissible Exposure Level (PEL) for chlorine dioxide vapor as 0.1 ppm. To understand this level of toxicity, it should be noted that elemental chlorine that has been used as a war gas, has a PEL that is five fold greater than that of chlorine dioxide.

SPBE has also been disclosed in U.S. Pat. Nos. 5,624,673, 5,653,983, and 5663,160 as an optional minor ingredient in topical formulations.

Other known topical formulations for treatment of hair loss are minoxodil, and a combination of minoxodil with tretinoin. The efficacy of minoxidil is limited as only a relatively small percentage of patients using it develope mild to moderate regrowth of hair. Further, Pharmacia and Upjohn, manufacturers of ROGAINE® minoxodil solution, warn that the most common side effect of minoxodil is itching and skin irritation of the treated area of the scalp. Tretinoin may also act as an irritant as indicated by the publication "Topical Tretinoin in Acne Therapy", by G.F. Webster, *Journal of the American Academy of Dermatology*, S38–S43, (1998).

A need exists for an SPBE formulation and method of preventing hair loss/promoting hair growth that exploits the merits of SPBE without requiring lengthy and hazardous pretreatment of the scalp. Especially needed is an SPBE formulation that offers enhanced effectiveness without causing scalp irritation.

SUMMARY OF THE INVENTION

The invention provides an improved preparation and a method for treating androgenetic alopecia. The preparation comprises an extract of saw palmetto berries containing phytosterols and a non-irritating compound to enhance the penetration of the extract into the follicles. More specifically, the improved low irritability topical preparation comprises saw palmetto berry extract containing phytosterols and one or more penetration enhancing constituents selected from the group consisting of adapalene, tretinoin gel microsponges, tretinoin and polyolprepolymer-2, retinaldehyde, tazarotene, salicylic acid, azelaic acid, and glycolic acid. Preferably the penetration enhancing constituents consist of one member selected from the group consisting of adapalene, tretinoin and polyolprepolymer-2, and tretinoin gel microsponges, and another member selected from the group consisting of salicylic acid and glycolic acid.

In another embodiment, the improved low irritability topical preparation comprises an active saw palmetto berry extract containing phytosterols, polyolprepolymer-2 and one or more penetration enhancing constituents selected from the group consisting of adapalene, tretinoin, retinaldehyde, tazarotene, salicylic acid, azelaic acid, and glycolic acid. Preferably the penetration enhancing constituents consist of one member selected from the group consisting of adapalene and tretinoin and another member selected from the group consisting of salicylic acid and glycolic acid.

Most preferably, in both of the above embodiments, the penetration enhancing constituents are adapalene and glycolic acid.

The preparations of the invention may include a vehicle suitable for topical application to the scalp in the form of a liquid, a gel, a foam, a styling hair tonic, a styling mousse, a styling hair spray, a pad dampened with a liquid, or any other means suitable for application to the scalp.

The method for the treatment of androgenetic alopecia comprises applying to the scalp a low irritability preparation comprising saw palmetto berry extract containing phytosterols, and one or more penetration enhancing constituents selected from the group consisting of adapalene, tretinoin gel microsponges, retinaldehyde, tazarotene, salicylic acid, azelaic acid, and glycolic acid. In another embodiment, the method for the treatment of androgenetic alopecia comprises applying to the scalp a low irritability preparation comprising saw palmetto berry extract containing phytosterols, polyolprepolymer-2 and one or more penetration enhancing constituents selected from the group consisting of adapalene, tretinoin, retinaldehyde, tazarotene, salicylic acid, azelaic acid, and glycolic acid.

DETAILED DESCRIPTION OF THE INVENTION

The present invention provides low irritability formulations of SPBE offering enhanced effectiveness in reducing hair loss by their greater ability to penetrate the pores of the scalp. In addition, there is provided by the invention a method for reducing hair loss by application to the scalp of a preparation comprised of the improved formulations.

The pilar cycle in humans is measured in years, typically two to four years. Consequently, a topical preparation to be effective in reducing hair loss or promoting hair growth must be used for extended periods of time. It is evident that a preparation or a method that causes irritation of the scalp often cannot be used for the time essential to be effective.

The SPBE constituent of the preparation of the invention may be obtained from a number of commercial sources. Satisfactory non-irritating SPBEs include Permixon® from P.F. Medicaments, Paris, France, SPBE from McZand Herbal Inc., Santa Monica, Calif., and others.

In a preferred embodiment of the preparation of the present invention, the SPBE constituent is the alcohol soluble material sold by Saw Palmetto Harvesting Company, Frostproof Fla. This SPBE is non-irritating when applied to the scalp. Typically, it has the following major components and concentrations:

| Phytosterols | |
|---|---|
| capesterol | about 0.01 to about 0.1 wt.wt. % |
| beta-sitosterol | about 0.1 to about 0.4 wt. % |
| stimasterol | about 0.01 to about 0.1 wt. % |
| Total sterols | greater than about 0.15 wt. % |
| Fatty Acids | |
| caprylic | about 1.0 to about 3.0 wt. % |
| capric | about 1.0 to about 3.0 wt. % |
| lauric | about 25 to about 32 wt % |
| cis-linoleic | about 3.0 to about 5.0 wt. % |
| linolenic | about 0.5 to about 1.5 wt. % |
| myristic | about 10 to about 1.5 wt. % |
| oleic | about 26 to about 35 wt. % |
| palmitic | about 7 to about 11 wt. % |
| stearic | about 1.0 to about 2.0 wt. % |

Other phytosterols, other fatty acids and other minor components may also be present without effecting the utility of the SPBE. The phytosterols are believed to be the active agents in the SPBE.

In another embodiment of the preparation of the present invention, all or a portion of the fatty acids have been removed from the above composition by further purification, as for example by extraction with aqueous alkaline solution. In this embodiment, the phytosterol composition of the SPBE is as follows:

| Phytosterols | |
|---|---|
| capesterol | greater than about 0.02 wt. % |
| beta-sitosterol | greater than about 0.2 wt. % |
| stimasterol | greater than about 0.02 wt. % |
| Total sterols | greater than about 0.3 wt. % |

The SPBE is present in the preparations of the invention in a concentration such that the concentration of pbytosterols in the total preparation is between about 0.01 wt. % and 1 wt. %. Preferably, the concentration of the SPBE is such that the concentration of the phytosterols in the total preparation is between about 0.01 wt. % and 0.5 wt. %. Most preferably the phytosterol concentration is about 0.10 wt. %.

The preparation of the invention comprises the SPBE and one or more penetration enhancing constituents selected from the group consisting of adapalene, tretinoin gel microsponges, retinaldehyde, tazarotene, salicylic acid, azelaic acid, and glycolic acid. In another embodiment, the preparation of the invention comprises the SPBE, polyolprepolymer-2 and one or more penetration enhancing constituents selected from the group consisting of adapalene, tretinoin, retinaldehyde, tazarotene, salicylic acid, azelaic acid, and glycolic acid.

Adapalene is a synthetic retinoid manufactured by Galderma having the following structural formula:

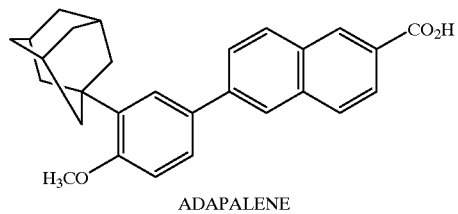

ADAPALENE

A research article by B. Shroot, "Pharmacodynamics and Pharmacokinetics of Topical Adapalene", *Journal of the American Academy of Dermatology*, S17–24, (1998) has shown that adapalene has several useful properties. First, adapalene has significant comedolytic activity, that is, it opens comedones or clogged pores. In the preparation of the invention, adapalene acts to enhance the effectiveness of the SPBE. Second, a 0.1 wt. % adapalene gel has a low irritative potential only slightly greater than a petroleum jelly control. Third, adapalene has anti-inflammatory effects both in vitro and in vivo. Each of these documented properties provides superiority to the preparations of the invention over the SPBE formulations of the prior art. Lastly, as adapalene is a retinoid, it may be expected to have direct benefits on stimulating hair regrowth.

Adapalene is present in a preparation of the invention in a concentration from about 0.01 wt. % to about 1 wt. %. Preferably, the adapalene concentration is from about 0.05 wt. % to about 0.5 wt. %. Most preferably, the adapalene concentration is about 0.1 wt. %.

Tazarotene is a retinoid having the following structural formula:

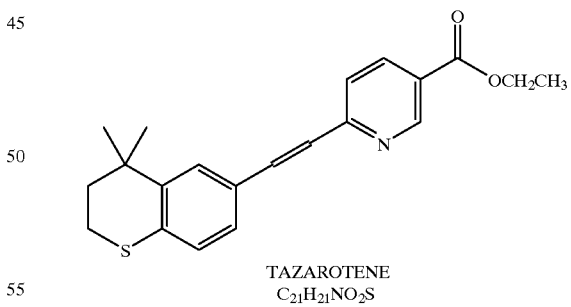

TAZAROTENE
$C_{21}H_{21}NO_2S$

Pharmacologically, tazarotene normalizes keratinocyte differentiation and minimizes proliferation of keratinocytes. These actions serve to inhibit microcomedo formation and prevent follicular plugging. Tazarotene also decreases epidermal inflammation and has been shown to down-regulate biochemical markers of inflammation. In the preparation of the invention, tazarotene acts to enhance the effectiveness of the SPBE.

Tazarotene is present in a preparation of the invention in a concentration from about 0.01 wt. % to about 1 wt. %.

Preferably, the tazarotene concentration is from about 0.02 wt. % to about 0.2 wt. %. Most preferably, the tazarotene concentration is about 0.05 to 0.1 wt. %.

Glycolic acid, a naturally occurring a-hydroxy acid has the formula:

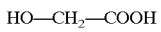

HO—CH$_2$—COOH

Glycolic acid been shown to exfoliate the stratum corneum. In the preparation of the invention, glycolic acid acts to enhance the effectiveness of the SPBE by increasing its penetration. Additionally, a research article by N. V. Perricone et al, "Photoprotective and Anti-inflammatory Effects of Topical Glycolic Acid", *Dermatological Surgery*, 22, 435–437 (1996) has shown glycolic acid acts as both a photoprotective agent and as an anti-inflammatory. These photoprotective and anti-inflammatory properties lend superiority to the preparations of the invention over the SPBE formulations of the prior art. Glycolic acid is present in a preparation of the invention in a concentration from about 0.1 wt. % to about 20 wt. %. Preferably, the glycolic acid concentration is from about 0.5 wt. % to about 10 wt. %. Most preferably, the glycolic acid concentration is about 5 wt. %.

Tretinoin has been used in acne therapy and in combination with minoxodil for the prevention of hair loss. Tretinoin is all-trans retinoic acid, also known as (all E) 3,7-dimethyl-9-(2,6,6-trimethyl-1-cyclohexen-1-yl)-2,4,6,8,-nonatetraenoic acid having the following structural formula:

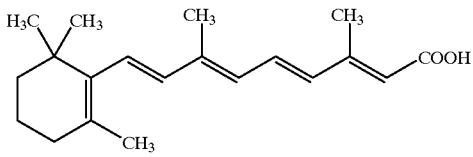

Tretinoin inhibits comedo formation and enhances comedolysis. Thus, it acts to prevent pores from becoming clogged and enhances removal of debris from clogged pores. There is also evidence that tretinoin itself increases hair growth factors. Additionally, a new form of topical tretinoin, RETIN-A MICRO®, has become available from Ortho Dermnatological, Raritan N.J. in which 0.1 wt. % of tretinoin is entrapped in a microscopic particle termed a "microsponge". This particle localizes to the follicle after topical application and then releases tretinoin. The slow release minimizes irritation. By virtue of their increased effectiveness and low irritation potential, a preparation of the invention containing tretinoin in the form of gel microsponges is superior to SPBE preparations of the prior art. Tretinoin is present in a preparation of the invention in a concentration from about 0.005 wt. % to about 0.2 wt. %. Preferably tretinoin concentration is from about 0.025 wt. % to about 0.1 wt. %.

Retinaldehyde is the aldehyde analog of retinoic acid having a terminal aldehyde group in place of the carboxyl group of retinoic acid. It has been shown by J. W. Fluhr et al, *Dermatology*, 199, Suppl 1:57–60 (1999) that retinaldehyde is significantly less irritating than retinoic acid (tretinoin). It is expected to be equally as effective in increasing the absorption of SPBE as is tretinoin. Incorporation of retinaldehyde in the SPBE preparations of the invention provides superior effectiveness and lower irritation potential of these preparations over the SPBE formulations of the prior art. Retinaldehyde is present in a preparation of the invention in a concentration from about 0.01 wt. % to about 1.0 wt. %. Preferably the retinaldehyde concentration is from about 0.05 wt. % to about 0.5wt. %. Most preferably, the retinaldehyde concentration is about 0.1 wt. %.

Azelaic acid, also known as 1,7 heptanedicarboxylic acid has the formula:

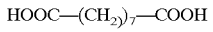

HOOC—(CH$_2$)$_7$—COOH

This agent has been shown to have antibacterial, antikeratinizing and anti-inflammatory properties. Thus, its use leads to a reduction in thickness of the strateum corneum or top layers of the skin, while preventing the formation of microcomedones or plugged follicles. These effects allow for increased penetration of SPBE into follicles while causing little, if any, irritation. Azeleic acid has been shown to cause less irritation than tretinoin. Incorporation of azeleic acid in the SPBE preparations of the invention provides superior effectiveness and lower irritation potential of these preparations over the SPBE formulations of the prior art.

Azeleic acid is present in a preparation of the invention in a concentration from about 0.1 wt. % to about 40 wt. %. Preferably, the azeleic acid concentration is about 20 wt. %.

It has been shown by M. C. Spellman et al, *Clinical Therapy*, 20(4m , 711–721 (1998) that a combination of azelaic acid and glycolic acid is less irritating than tretinoin and equally as effective in treating facial acne. As both azeleic acid and glycolic acid lead to a reduction in the thickness of the stratum corneum, and both have anti-inflammatory properties, this combination increases the absorption of topically applied SPBE while causing less irritation than prior art compounds.

Accordingly, incorporation of azelaic acid and glycolic acid in the SPBE preparations of the invention provides superiority of these preparations over prior art SPBE formulations.

Azelaic and glycolic acids are present in a preparation of the invention in relative proportions ranging from about 10:90 azelaic:glycolic to about 90:10 azelaic:glycolic. The total concentration of azelaic plus glycolic acids in a preparation of the invention is from about 0.1 wt. % to about 40 wt. %. Preferably, the azelaic plus glycolic acid concentration is about 20 wt%.

Salicylic acid (2-hydroxy benzoic acid) is a beta hydroxy acid having the formula:

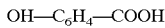

OH—C$_6$H$_4$—COOH

Salicyclic acid is used topically in numerous products to reduce scaling. It is well known as a keratolytic and has been used in combination with glycolic acid to aid in comedolysis or the opening of clogged follicles. It increases the penetration of SPBE into follicles and has a low irritancy potential. Incorporation of salicylic acid in the SPBE preparations of the invention provides superiority of these preparations over the SPBE formulations of the prior art.

Salicyclic acid is present in a preparation of the invention in a concentration from about 0.1 wt. % to about 10 wt. %. Preferably, the salicyclic concentration is between about 1% wt. % and 3 wt%.

Polyolprepolymer-2 is a urethane compound of molecular weight up to about 200,000 which is prepared by reacting approximately two moles of a hydroxy terminated linear alkylene or polyalkylene glycol or polyether with approximately one mole of a monomeric organic diisocyanate as described in U.S. Pat. No. 5,700,483, the entirety of which is incorporated by reference herein. Preferably, polyolprepolymer-2 has average molecular weight of about 4000 and is prepared by reacting about one mole of dicyclohexylmethanediisocyanate with about two moles of propylene glycol 725.

Incorporation of polyolprepolymer-2 in a topical formulation has been shown to have the characteristic of moderating the rate of transmission of a retinoid to the skin. Specifically, it has been shown that formulations incorporating tretinoin and polyolprepolymer-2 are significantly less irritating and exhibit therapeutically equally efficacy to identical formulations without polyolprepolymer-2. When polyolprepolymer-2 is present in a preparation of the invention, tretinoin need not be in the form of gel microsponges. Incorporation of the polyolprepolymer-2 in the SPBE preparations of the invention provides superiority of these preparations over the SPBE formulations of the prior art. The polyolprepolymer-2 is present in a preparation of the invention in a concentration from about 1 wt% to about 20 wt%. Preferably, the polyolprepolymer-2 is present in a concentration from about 2 wt% to about 15 wt%.

The preparations of the invention may include a vehicle for the application to the scalp such as a liquid, a gel, a foam, a styling mouse, a styling gel, a styling hair tonic, a styling hair spray a lotion, a pad dampened with a liquid, or any other means suitable for application to the scalp. Preferably the SPBE preparations of the invention are employed as a liquid or as a gel. Most preferred is a gel.

The formulation of all such topical vehicles is well known to those skilled in the art. A suitable topical vehicle for formulation of the SPBE preparation as a liquid includes ethanol, isopropanol, their mixtures in all proportions. To prepare a liquid preparation of the invention, the SPBE and the penetration enhancing constituents are dissolved or dispersed in the alcohol constituents with agitation.

Elevated temperatures may be used to facilitate the dispersion process.

An example of a suitable topical vehicle for formulation of the SPBE preparation as a gel is:

| Component | wt % |
|---|---|
| hydroxypropylcellulose | 2.1 |
| 70/30 isopropyl alcohol/water | 90.9 |
| propylene glycol | 5.1 |
| Polysorbate 80 | 1.9 |

To prepare a gel preparation of the invention, the 70% isopropanol and the propylene glycol are first combined. The SPBE and the penetration enhancing constituents are dispersed in the alcohols with agitation. The hydroxypropylcellulose and the Polysorbate 80 are then incorporated with mixing until a gel results.

An example of a suitable topical vehicle formulation for formulation of the SPBE preparation as a foam is:

| Component | wt % |
|---|---|
| cetyl alcohol | 1.1 |
| stearyl alcohol | 0.5 |
| Quaternium 52 (52%) | 1.0 |
| propylene glycol | 2.0 |
| Ethanol 95 PGF3 | 61.05 |
| deionized water | 30.05 |
| P75 hydrocarbon propellant | 4.30 |

To prepare a foam preparation of the invention, the SPBE and the penetration enhancing constituents are first dispersed in the ethanol at elevated temperature. The cetyl and stearyl alcohols are added to the heated dispersion and mixed until dissolved. The Quaternium 52, the propylene glycol and water are added and stirred until homogeneous while maintaining elevated temperature. The mixture is cooled and dispensed into an aerosol can. A valve is fitted to the can and the can is then charged with the propellant.

A suitable topical vehicle for formulation of the SPBE preparation as a hair grooming tonic is the formulation of Example VI of U.S. Pat. No. 5,997,853, the entirety of which is incorporated by reference herein. The SPBE and the penetration enhancing constituents are first incorporated in the ethanol constituent and the remaining components are added and incorporated by mixing together in a conventional manner.

A suitable topical vehicle for formulation of the SPBE preparation as a styling mousse is the formulation of Example XIII of U.S. Pat. No. 5,997,853. The SPBE and the penetration enhancing constituents are first incorporated in the ethanol constituent. Then, the remaining components except the isobutane are added, and blended together at ambient temperature until well mixed. Aluminum aerosol cans are filled with 95 parts of this batch, a valve is fitted to the can and lastly pressure filled with 5 parts isobutane.

A suitable topical vehicle for formulation of the SPBE preparation as a styling hair spray is the formulation of Example XIV of U.S. Pat. No. 5,997,853. The SPBE and the penetration enhancing constituents are first incorporated in the ethanol. The remaining ingredients are then added and mixed in a conventional manner.

The mode of use of a SPBE preparation of the invention is application of 1 cc of the preparation to the affected area of the dry scalp twice a day for a period of four months. The preparation should be massaged into the scalp and remain in place or at least four hours before washing, rinsing or showering. After the four month initial period, a sustaining application of 1 cc once a day is used.

The following examples are presented to provide a more complete understanding of the invention. The specific techniques, conditions, materials, and proportions set forth to illustrate the principles and practice of the invention are exemplary and should not be construed as limiting the scope of the invention.

EXAMPLES

Examples 1–14

Tables I and II below provide examples of preparations of the invention. The SPBE in this table is provided by Saw Palmetto Harvesting Company, Frostproof, Fla. and has a phytosterol concentration of 0.16 wt. %. The topical vehicle may be chosen appropriate to the use of the preparation as a liquid a gel, a foam, a styling mousse, a styling hair tonic, a styling hair spray, a pad dampened with a liquid, or any other means suitable for application to the scalp. All percentages are by weight.

TABLE I

| Constituent | Ex. 1 | Ex. 2 | Ex. 3 | Ex. 4 | Ex. 5 | Ex.6 | Ex. 7 |
|---|---|---|---|---|---|---|---|
| SPBE, % | 31.25 | 40.0 | 60.0 | 80.0 | 31.25 | 31.25 | 31.25 |
| adapalene, % | 0.1 | — | — | — | — | — | — |
| glycolic acid % | — | 5.0 | — | — | — | — | — |
| tretinoin (as gel microsponges), % | — | — | 0.025 | — | — | — | — |
| retinaldehyde, % | — | — | — | 0.1 | — | — | — |

TABLE I-continued

| Constituent | Ex. 1 | Ex. 2 | Ex. 3 | Ex. 4 | Ex. 5 | Ex. 6 | Ex. 7 |
|---|---|---|---|---|---|---|---|
| azelaic acid, % | — | — | — | — | 20 | — | — |
| tazarotene, % | — | — | — | — | — | 0.1 | — |
| salicylic acid, % | — | — | — | — | — | — | 2.0 |
| Topical Vehicle | Balance | Balance | Balance | Balance | Balance | Balance | Balance |

TABLE II

| Constituent | Ex. 8 | Ex. 9 | Ex. 10 | Ex. 11 | Ex. 12 | Ex. 13 | Ex. 14 |
|---|---|---|---|---|---|---|---|
| SPBE, % | 31.25 | 31.25 | 31.25 | 31.25 | 31.25 | 31.25 | 31.25 |
| adapalene, % | 0.05 | 0.05 | — | — | — | — | — |
| glycolic acid, % | 5.0 | — | 1.0 | 5.0 | — | 5.0 | 5.0 |
| tretinoin, % | — | — | 0.025 | — | 0.1 | — | 0.05 |
| retinaldehyde, % | — | — | — | 0.1 | — | — | — |
| azelaic acid, % | — | — | — | 15 | 10 | — | — |
| tazarotene, % | — | — | — | — | — | 0.1 | — |
| salicylic acid, % | — | 2.0 | — | — | — | — | — |
| polyolprepolymer-2, % | 10 | 10 | 10 | 10 | 10 | 10 | 10 |
| Topical Vehicle | Balance | Balance | Balance | Balance | Balance | Balance | Balance |

Examples 15–21

Table III below provides examples of preparations of the invention. The SPBE in this table has been purified from the SPBE provided by Saw Palmetto Harvesting Company, Frostproof, Fla. by extraction with an aqueous alkaline solution and has a phytosterol concentration of 0.5 wt%. The topical vehicle may be chosen appropriate to the use of the preparation as a liquid, a gel, a foam, a styling mousse, a styling hair tonic, a styling hair spray, a pad dampened with a liquid, or any other means suitable for application to the scalp. All percentages are by weight.

TABLE III

| Constituent | Ex. 15 | Ex. 16 | Ex. 17 | Ex. 18 | Ex. 19 | Ex. 20 | Ex. 21 |
|---|---|---|---|---|---|---|---|
| SPBE, % | 15.0 | 20.0 | 30.0 | 10.0 | 10.0 | 10.0 | 10.0 |
| adapalene, % | 0.05 | 0.05 | — | — | — | — | — |
| glycolic acid, % | 5.0 | — | 1.0 | 5.0 | — | 5.0 | 5.0 |
| tretinoin, % | — | — | 0.025 | — | 0.1 | — | 0.05 |
| retinaldehyde, % | — | — | — | 0.1 | — | — | — |
| azelaic acid, % | — | — | — | 15 | 10 | — | — |
| tazarotene, % | — | — | — | — | — | 0.1 | — |
| salicylic acid, % | — | 2.0 | — | — | — | — | — |
| polyolprepolymer-2, % | 10 | 10 | 10 | 10 | 10 | 10 | 10 |
| Topical Vehicle | Balance | Balance | Balance | Balance | Balance | Balance | Balance |

What is claimed is:

1. A low irritability topical preparation for the treatment of hair loss comprising:

(A) saw palmetto berry alcohol extract containing phytosterols;

(B) one or more members of the group consisting of adapalene; retinaldehyde, tazarotene, salicyclic acid, glycolic acid and azelaic; and (C) polyoprepolymer-2.

2. The preparation of claim 1 which further comprises a member of the group consisting of tretinoin and tretinoin gel microsponges.

3. A topical preparation according to claim 1 containing the combination of adapalene and glycolic acid.

4. A topical preparation according to claim 1 containing polyolprepolymer-2 and a member of the group consisting of salicylic acid and glycolic acid.

5. A topical preparation according to claim 1 comprising salicylic acid or glycolic acid together with adapalene and further comprising tretinoin gel microsponges.

6. A topical preparation as recited by claim 1, wherein the concentration of phytosterols in the preparation ranges from about 0.01 wt.% to about 1 wt.%.

7. A topical preparation as recited by claim 1, wherein the concentration of phytosterols in the preparation ranges from about 0.01 wt.% to about 0.5 wt.%.

8. A topical preparation as recited by claim 1, wherein the adapalene concentration ranges from about 0.01 wt.% to about 1 wt.%.

9. A topical preparation as recited by claim 1, wherein the glycolic acid concentration ranges from about 0.1 wt.% to about 20 wt.%.

10. A topical preparation as recited by claim 1, wherein the tretinoin concentration in the form of gel microsponges ranges from about 0.005 wt.% to about 0.2 wt.%.

11. A topical preparation as recited by claim 1, wherein the retinaldehyde concentration ranges from about 0.01 wt.% to about 1.0 wt.%.

12. A topical preparation as recited by claim 1, wherein the azelaic acid concentration ranges from about 0.1 wt% to about 40 wt.%.

13. A topical preparation as recited in claim 1, wherein the total concentration of azelaic acid and glycolic acid ranges from about 0.1% to about 40%.

14. A topical preparation as recited in claim 1, wherein the proportion of azelaic acid to glycolic acid ranges from about 10:90 to about 90:10.

15. A topical preparation as recited by claim 1, wherein the tazarotene concentration ranges from about 0.01 wt.% to about 1.0 wt.%.

16. A topical preparation as recited by claim 1, wherein the salicylic acid concentration ranges from about 0.1 wt.% to about 10 wt.%.

17. A topical preparation as recited by claim 1, wherein the preparation further contains a topical vehicle for application to the scalp selected from the group consisting of liquid, gel, foam, styling mousse, styling hair tonic and styling hair spray.

18. A method for the treatment of male pattern hair loss, comprising applying to the scalp a low irritability preparation comprising saw palmetto berry alcohol extract containing phytosterols; and one or more penetration enhancing constituents selected from the group consisting of adapalene, tretinoin, retinaldehyde, tazarotene, salicylic acid, azelaic acid, and glycolic acid; polyolprepolymer-2; and, optionally, tretinoin gel microsponges.

* * * * *